(12) United States Patent
Carriazo

(10) Patent No.: US 6,447,526 B1
(45) Date of Patent: Sep. 10, 2002

(54) DISPOSABLE MICROKERATOME BLADE HOUSING

(75) Inventor: Cesar C. Carriazo, Kra 59B No. 79-261, Barranquilla (CO)

(73) Assignees: Cesar C. Carriazo, Barranquilla (CO); LouLou Corporation N.V., Curacao (AN)

(*) Notice: Subject to any disclaimer, the term of this patent is extended or adjusted under 35 U.S.C. 154(b) by 0 days.

(21) Appl. No.: 09/533,350

(22) Filed: Mar. 23, 2000

Related U.S. Application Data

(60) Provisional application No. 60/125,845, filed on Mar. 24, 1999.

(51) Int. Cl.⁷ .................................................. A61F 9/00
(52) U.S. Cl. .......................... 606/166; 606/1; 606/108; 606/167
(58) Field of Search .......................... 606/1, 108, 166, 606/167; 604/22; 30/272.1, 276, 287, 293, 259–362

(56) References Cited

U.S. PATENT DOCUMENTS

| | | | |
|---|---|---|---|
| 4,173,980 A | 11/1979 | Curtin | 128/303 |
| 4,660,556 A | 4/1987 | Swinger et al. | 128/305 |
| 4,662,370 A | 5/1987 | Hoffman et al. | 128/305 |
| 4,665,914 A | 5/1987 | Tanne | 128/305 |
| 4,674,503 A | 6/1987 | Peyman et al. | 128/305 |
| 4,688,570 A | 8/1987 | Kramer et al. | 128/305 |
| 4,840,175 A | 6/1989 | Peyman | 128/303.1 |
| 5,133,726 A | 7/1992 | Ruiz et al. | 606/166 |
| 5,586,980 A | 12/1996 | Kremer et al. | 606/4 |
| RE35,421 E | 1/1997 | Ruiz et al. | 606/166 |
| 5,591,174 A | 1/1997 | Clark et al. | 606/130 |
| 5,591,185 A | 1/1997 | Kilmer et al. | 606/166 |
| 5,595,570 A | 1/1997 | Smith | 606/166 |
| 5,624,456 A | 4/1997 | Hellenkamp | 606/166 |
| 5,980,543 A | 11/1999 | Carriazo et al. | 606/166 |
| 6,051,009 A * | 4/2000 | Hellenkamp et al. | 606/166 |
| 6,083,236 A * | 7/2000 | Feingold | 606/166 |
| 6,228,099 B1 * | 5/2001 | Dybbs | 606/166 |

FOREIGN PATENT DOCUMENTS

| | | | |
|---|---|---|---|
| EP | 0771553 | 10/1996 | A61F/9/00 |

* cited by examiner

*Primary Examiner*—Danny Worrell
*Assistant Examiner*—Shaun R. Hurley
(74) *Attorney, Agent, or Firm*—Bracewell & Patterson, L.L.P.

(57) ABSTRACT

An apparatus which attaches to microkeratome surgical devices. The disposable microkeratome blade housing apparatus securely attaches to the surgical devices but remains independent of the motor, gearing and cutting head components. In a first embodiment, the blade housing includes a knife edged blade, a blade holder, plaque and flexible coupling structure. The snap tight coupling structure provides a self-positioning, secure attachment of the housing to existing compatible and accommodating microkeratomes. In a second embodiment, the blade housing and cutting head are integral and include a knife edged blade, a blade holder, and a plaque. The blade housing/cutting head combination of the second embodiment is entirely disposable and fixedly secured to said motor. In both embodiments, the blade holder is acted upon by the motor and gearing to oscillate the blade holder in the housing. As the microkeratome advances over the eye, the plaque portion of the housing partially compresses the cornea just ahead of the blade. The partial compression produced by the plaque along with the blade define the shape and depth of the corneal resection. The disposable blade housing is fabricated from materials selected from a group consisting of polymers, composites and ceramics.

15 Claims, 4 Drawing Sheets

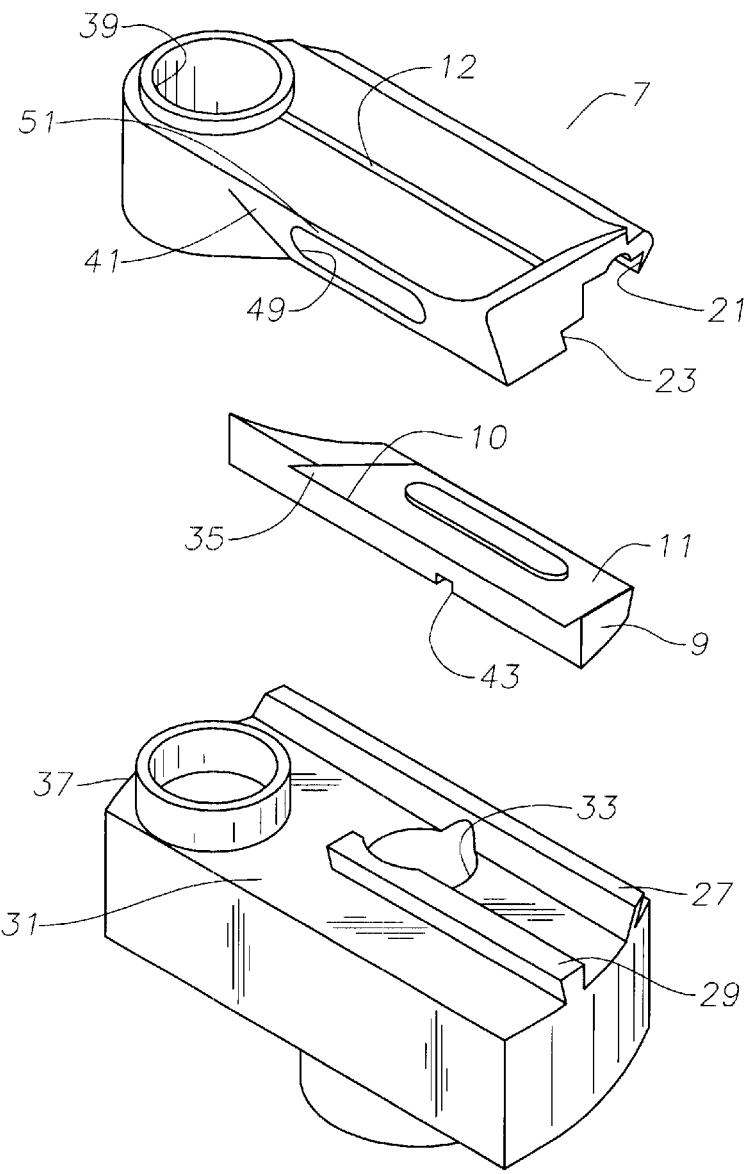
Fig. 4
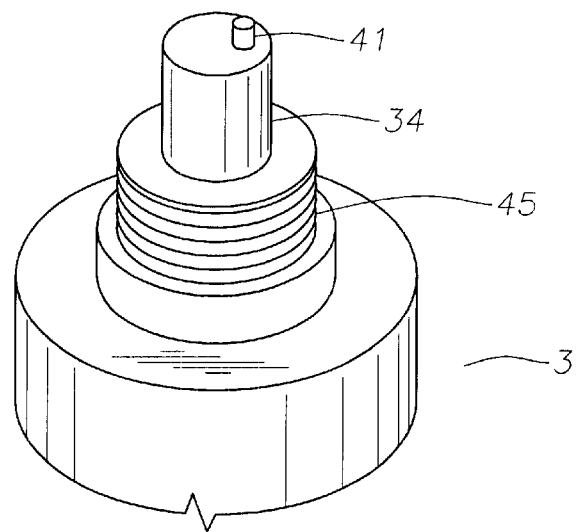

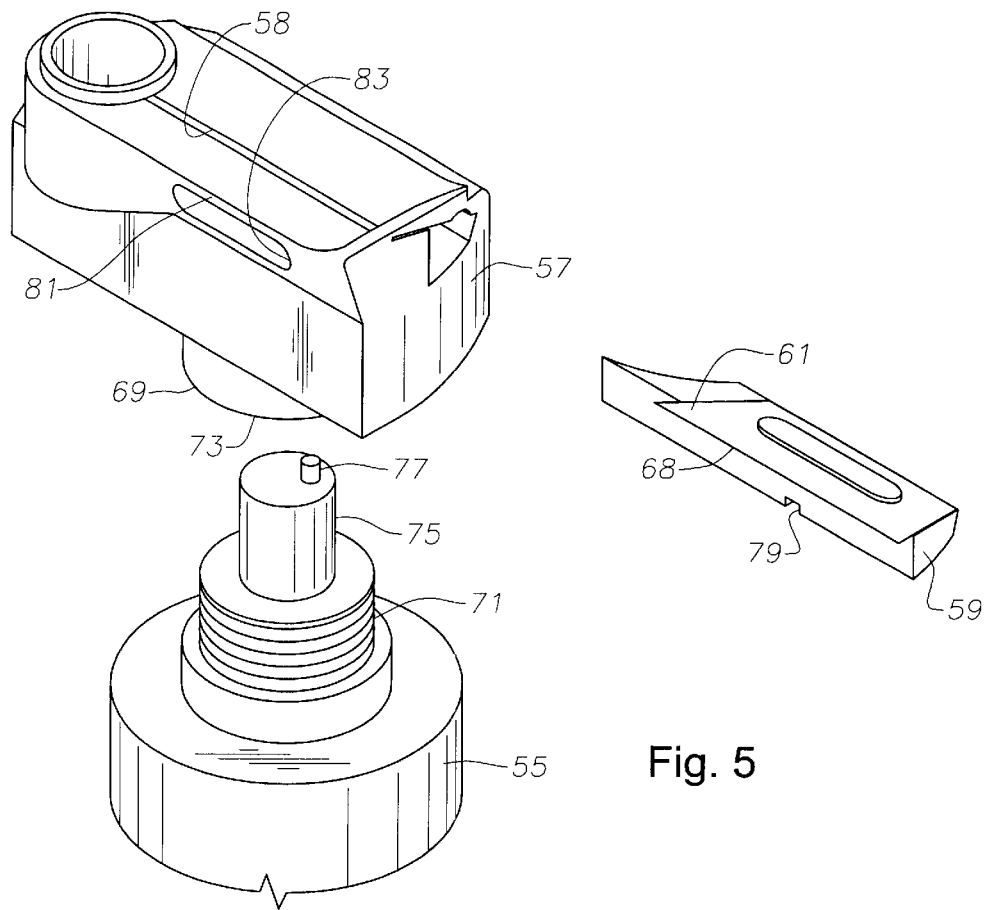
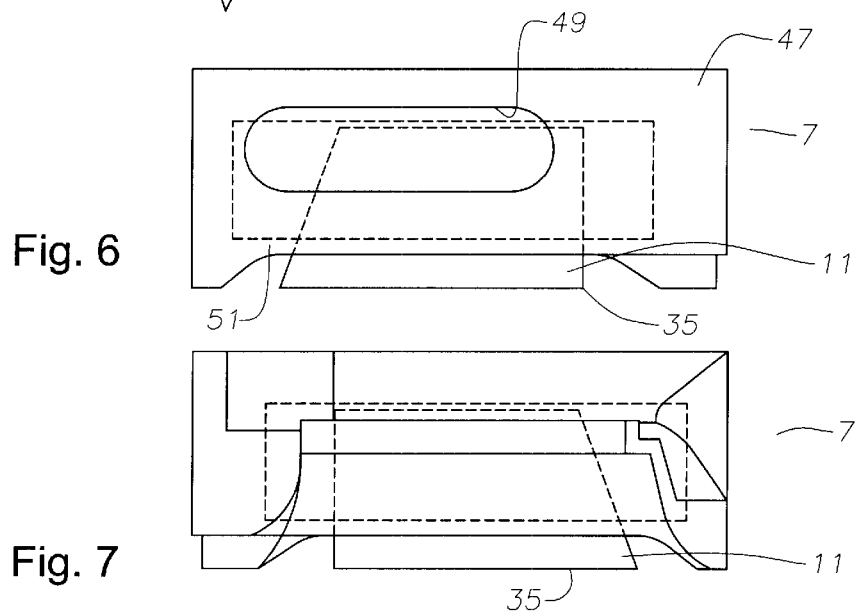
Fig. 5
Fig. 6
Fig. 7

US 6,447,526 B1

DISPOSABLE MICROKERATOME BLADE HOUSING

This application claims the benefits of provisional application Ser. No. 60/125,845, filed Mar. 24, 1999.

BACKGROUND OF THE INVENTION

1. Field of Invention

The present invention relates generally to surgical instruments and in particular to instruments for surgery of the eye.

More particularly, the present invention relates to medical instruments used for lamellar keratotomy, known as microkeratomes.

Specifically, the present invention is an improvement to existing microkeratomes in that the invention is disposable thereby replacing the permanent cutting head portion of the existing instruments and increasing the efficiency of the microkeratome by increasing the efficiency of operations through the elimination of timely de-contamination procedures on current microkeratomes.

2. Description of the Prior Art

In the field of eye surgery generally, and in the field of keratectomy specifically, a number of devices called microkeratomes have been developed. The microkeratome surgical instrument is used to perform lamellar keratotomy. During the lamellar keratotomy operation, the instrument produces a thin section of the cornea, on which further surgery may be performed. In order to produce the thin section, the instrument must be moved across the ocular globe or eye. The microkeratome excursion may be linear or rotational across the ocular globe. In order to move the instrument a number of means have been utilized including manual, a track and gears or through use of a keyed pivot sweeping the instrument through an arc.

Microkeratomes are comprised of numerous delicate and precision parts. In general, these medical instruments typically differ in their configuration, although having a number of common features. The common features include a vacuum ring to securely grip the ocular globe, a cutting head that includes a plaque and knife edged blade to compress and cut the ocular globe, and a motor/gearing combination that both oscillates the blade and moves the instrument over a given path with respect to the ocular globe.

One configuration in the prior art discloses a microkeratome assembled such that the motor and gearing are directly connected and combined in a common housing or a permanently attached individual housing. The motor and gearing unit is then permanently attached to a cutting head which accommodates the blade. Another configuration disclosed in the prior art utilizes the common features of a motor/gearing combination but accommodates the components in separable housings. Separate accommodations for the motor and gearing requires the combination of the gearing and blade in the cutting head. Each of the configurations described have their individual disadvantages and some common problems.

The configuration uniting the gearing with the motor in a single housing with a permanent attachment to the cutting head also includes a cutting head designed to allow access and removal of the blades. Although the cutting head can be opened to replace the blades, the surface through which the blade protrudes for providing cutting is hinged but does not detach from the cutting head. Since the instrument is ostensibly a single unit with motor, gearing, and cutting head, after each use the entire instrument must endure a sterilization process. Due to the delicate and intricate nature of the instrument, sterilization can be deleterious to the precision gearing and electronics. Therefore the importance of the elimination or reduction in the number of sterilizations is apparent.

Separation of the gearing and motor does not completely solve the instrument sterilization problem. Combining the gearing and cutting head into a removable unit obviates the need to process the motor and electronics with the well known methods of sterilization; however, the complexity and size of the cutting head is increased. In addition, the amount of space available around the ocular globe is limited and restricted by the patient's anatomy. Thus, while the life of the motor and electronics may be extended, some patients may not be able to accommodate the size of the instrument. Also, unless the entire cutting head assembly is discarded after use, which may be cost prohibitive, the delicate precision gearing is exposed to the sterilization process after each use.

Another consideration fundamental to this type of surgery is the integrity or quality of the cut. Discontinuities or aberrations in the shape of the cut can have serious ramifications on the post-operative vision of the patient. Prior art discloses microkeratomes with characteristics negatively affecting the quality or integrity of the cut. Some of the negative characteristics are poor material properties and compliance, or lack of rigidity of the assembled instrument. The construction of microkeratome components from such materials with unacceptable properties can result in degraded performance for a variety of reasons including dimensional instability. Dimensional instability, such as warping of the cutting head, allows the blade to move in an unplanned manner, which results in an unintended cut shape. Excessive compliance of the assembled microkeratome may result in unintended excursion from the desired path over the ocular globe. Consequently with diminished control of the cutting instrument the quality of the cut is compromised.

In response to the shortcomings described herein, it is a feature of the present invention to provide an improvement to existing microkeratomes wherein the disposable blade housing is independent of the motor, gearing, and cutting head of the microkeratome.

It is another feature that the disposable blade housing improves existing microkeratomes by remaining dimensionally stable, damping vibration and resisting deflection while maintaining the quality of the cut.

It is a further feature that the disposable blade housing improves on existing microkeratome requirements of preoperative assembly of the instrument.

It is a still further feature that the disposable blade housing improves on the existing microkeratome requirements for sterilization and contamination potential of the surgery.

It is a further feature that the disposable blade housing improves existing microkeratome requirements by providing the disposable blade housing in a limited number of components, such that the overall number of parts are eliminated.

It is a further feature of the invention that the disposable blade housing is composed of materials to reduce the cost of the overall procedure.

SUMMARY OF THE INVENTION

The present invention is drawn to a disposable microkeratome for attachment to a guide ring secured to an ocular globe to perform lamellar keratotomy. The microkeratome has a blade assembly with a cutting edge. A cutting head is adapted to join to the guide ring and move in a plane substantially parallel to a surface of the guide ring. The cutting head has an integral compression surface for compressing the ocular globe and a blade slot adjacent the compression surface. The cutting head closely receives the blade assembly such that the cutting edge protrudes through the blade slot toward the compression surface and the blade assembly is restrained to move substantially only along one axis. A motor is releasably attached to the cutting head to osciallate the blade assembly along the one axis.

The cutting head has a lower portion releasably joined to an upper portion and the blade assembly is held between the upper portion and the lower portion. The upper portion has a longitudinal key and the lower portion has a longitudinal keyway adapted to receive the longitudinal key of the upper portion to hold the upper portion and lower portions together. The upper portion has a protrusion and the lower portion has an opening adapted to receive the protrusion and laterally restrain the lower portion with respect to the upper portion. The lower portion is made from a material that is more flexible than the material of the upper portion. The lower portion is a material selected from the group consisting of polymeric, composite, and ceramic materials. The cutting head has an overall height dimension and a height of the lower portion is less than one third the overall height dimension. The lower portion is located within two lower portion height dimensions of a point at which the lower portion joins the guide ring. The motor rotates a pin about a central axis and a blade assembly has a slot that receives the pin.

The invention also encompasses a method of performing lamellar keratotomy on an ocular globe including providing a microkeratome having an upper portion, a lower portion, and a blade. A guide ring is secured to the ocular globe and the microkeratome is joined to the guide ring. The microkeratome is moved across the guide ring to contact the blade with and cut the ocular globe. The microkeratome is removed from the guide ring and the lower portion and blade are disposed of Then, a fresh unused lower portion and blade are joined to the upper portion.

BRIEF DESCRIPTION OF THE DRAWINGS

FIG. 4 is an inferior exploded view of the first embodiment of the invention with the blade holder and motor.

FIG. 5 is an inferior exploded view of the second embodiment of the invention.

FIG. 6 is a front view of the disposable blade housing of the first embodiment.

FIG. 7 is a rear view of the disposable blade housing of the first embodiment.

DETAILED DESCRIPTION OF THE PREFERRED EMBODIMENTS

Figure 1:
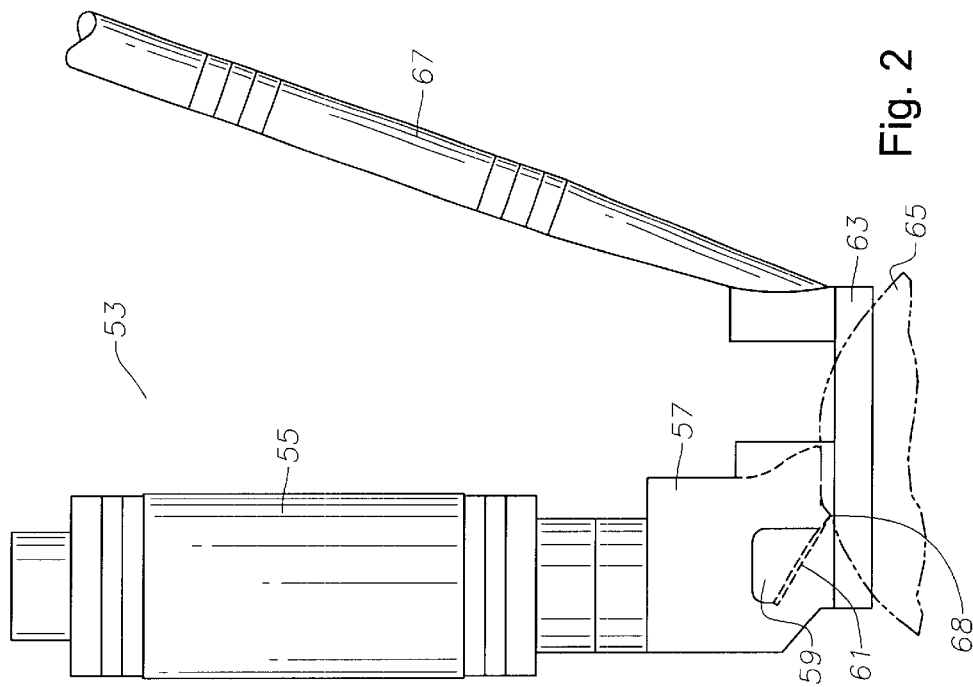
FIG. 1 is a side view of a microkeratome with the first embodiment of the present invention wherein the cutting head and disposable blade housing are separate components.
Figure 3:
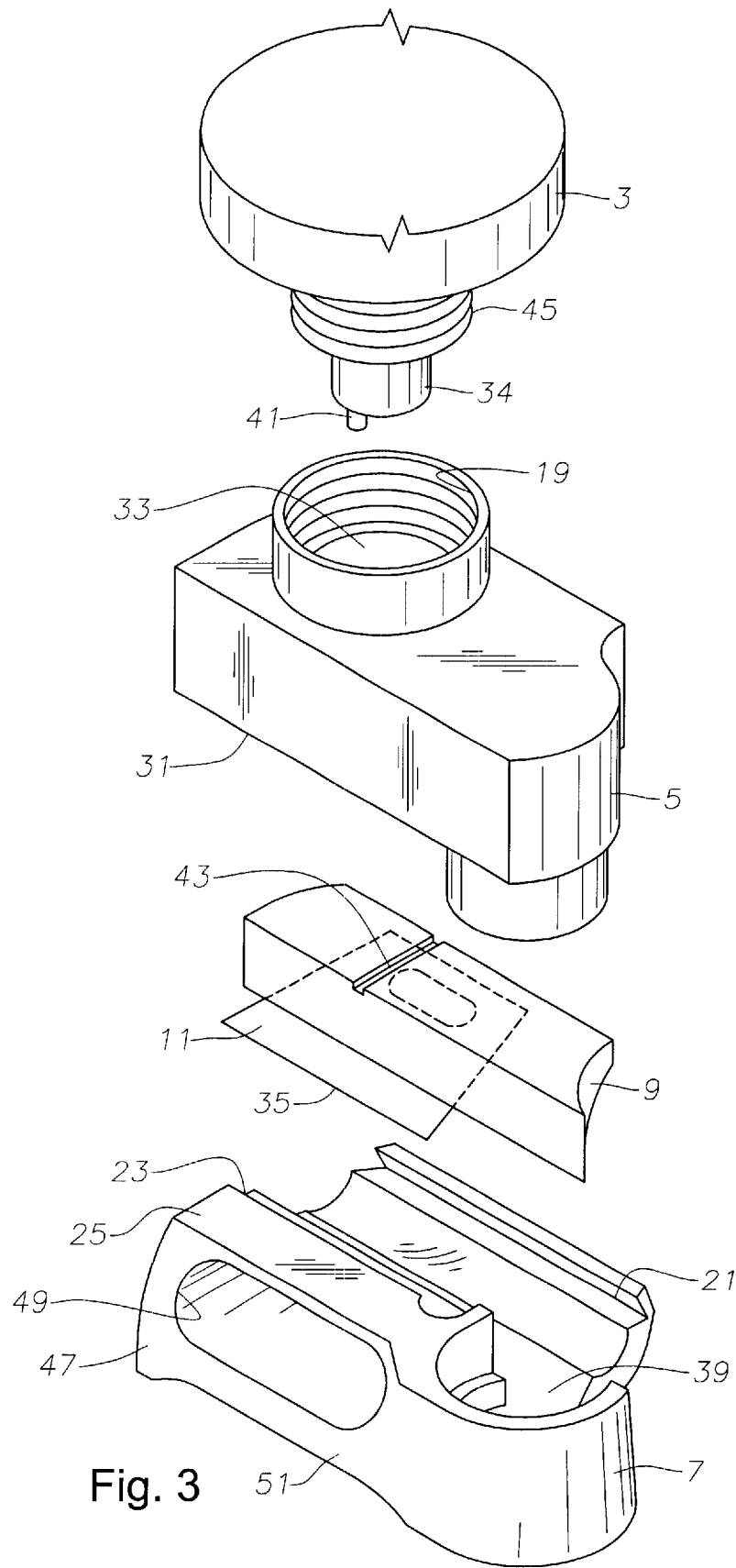
FIG. 3 is an superior exploded view of the first embodiment of the invention, shown together with the blade holder and motor.

In a first embodiment of the invention as seen in FIGS. 1, 3 and 4, microkeratome 1 comprises motor 3, cutting head 5, disposable blade housing 7, blade holder 9 and blade 11. Microkeratome 1 is engaged with guide ring 13 which surrounds ocular globe 15. The coupling of guide ring 13 and disposable blade housing 7 during actuation of microkeratome 1, typically composed of a gear and track system, is not shown. Other well-known coupling means may be employed during actuation of microkeratome 1 that are also not shown. Vacuum 17 is used to maintain ocular globe 15 above the plane of guide ring 13 for correct positional alignment with blade 11 for incision.

Cutting head 5 has threaded portion 19 for engagement with motor 3. Disposable blade housing 7 is interchangeably attached to cutting head 5 by a first and second longitudinal keyway 21, 23 located on superior portion 25 of disposable blade housing 7, which are respectively adapted to receive a first and second longitudinal key 27, 29 located on the inferior portion 31 of cutting head 5. Cutting head 5 has an axial opening 33 for receiving axial shaft 34 of motor 3.

Blade 11 has trapezoidal shape, the base 35 of which projects angularly outward from blade holder 9 towards portion of ocular globe above the plane of guide ring for incision during actuation of microkeratome. Blade 11 and blade holder 9 are closely received in housing 7 to move substantially along only one axis. A cutting edge 10 of blade 11 extends through a blade slot 12 in housing 7 toward plaque 51 described in more detail below. Cutting head 5 has cylindrical projection 37 to further engage disposable blade housing 7. Disposable blade housing 7 has a cylindrical opening 39 to mate with cylindrical projection 37 of cutting head 5. Opening 39 may also be adapted to receive a pin (not shown) extending upward from guide ring 13 to allow the apparatus to rotate the plane of ring 13.

Now referring to FIGS. 3 and 4, axial shaft 34 of motor 3 terminates outside blade holder 9 in small eccentric projection or pin 41. Eccentric pin 41 engages slot 43 of blade holder 9 through internally threaded portion 19 of cutting head 5 to transmit an oscillatory motion to blade 11 that corresponds to the speed of the motor 3. Motor 3 has corresponding threaded portion 45 for engagement with cutting head 5. Axial opening 33 of cutting head permits extension of axial shaft 34 therethrough. The eccentric pin 41 secures blade holder 9 loosely between cutting head 5 and disposable blade housing 7. Blade holder 9 thus oscillates freely in direct relation with axial shaft 19 and is held such that lateral movement of the blade holder 9 is permitted. On the advancing face 47 of disposable blade housing 7 is an elliptical opening 49. Elliptical opening 49 defines plaque 51 that compresses and maintains ocular globe 15 at a predetermined pressure for incision thereto during actuation of microkeratome 1 as can be seen in FIG. 5.

Figure 2:
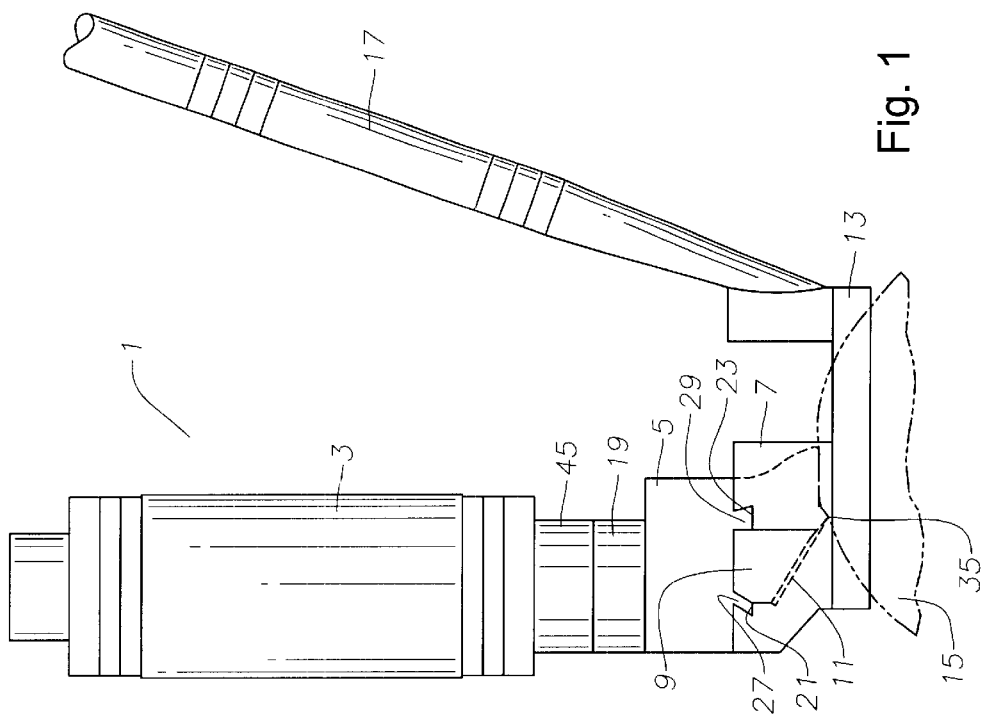
FIG. 2 is side view of a second embodiment of the present invention wherein the disposable blade housing and cutting head are a single component.

FIGS. 2 and 5 show microkeratome 53 in a second embodiment of the present invention. In this embodiment, microkeratome 53 comprises motor 55, disposable blade housing 57, blade holder 59 and blade 61. Microkeratome 53 is engaged with guide ring 63 which surrounds ocular globe 65 in the same manner as in the first embodiment. Vacuum 67 is used to maintain ocular globe 65 above the plane of the guide ring 63 for correct positional alignment with blade 61 for incision.

Disposable blade housing 57 is adapted to receive blade holder 59 which has blade 61 fixedly attached thereto such that blade 61 and holder 59 move substantially only along one axis. Blade 61 is trapezoidal with the cutting edge 68 of blade 61 projecting angularly outward from disposable blade housing 57 through blade slot 58 toward plaque 83 and a portion of ocular globe 65 above the plane of guide ring 63.

Superior threaded portion 69 of disposable blade housing 57 is adapted to receive corresponding threaded portion 71 from motor 55. Disposable blade housing 57 has axial opening 73 in alignment with axial shaft 75 of motor 55. As in the first embodiment, axial shaft 75 of motor 55 terminates in eccentric pin 77, which engages slot 79 of blade holder 59 and secures blade holder 59 within disposable blade housing 57. Operation of motor 55 oscillates blade holder 59 and blade 61 during actuation of microkeratome 53.

As in the first embodiment, during actuation of microkeratome 53 across a predetermined cutting path, disposable blade housing 57 has plaque 81 formed by elliptical opening 83 that compresses and maintains ocular globe 65 at a predetermined pressure for incision thereto.

The microkeratome blade housing of the present invention includes a lockable and releasable coupling capable of snap tight fit between the disposable blade housing and the remaining part of a microkeratome. The coupling provides a self-positioning and secure placement of the disposable blade housing onto the medical instrument such that once the disposable blade housing is in place there is no relative movement between the medical instrument and the disposable blade housing.

The disposable blade housing includes structure capable of transmitting forces from the motor and gearing to the blade. The transmitted forces induce a reciprocating or oscillating motion on the blade. The blade is constrained to oscillate or reciprocate in the direction transverse to the direction of motion of the microkeratome. Overall structural rigidity of the instrument is maintained by the disposable blade housing height dimension being preferably less than one third the overall height dimension of the assembled microkeratome. Positioning of the disposable blade housing is also controlled. The disposable blade housing is preferably located within two disposable blade housing height dimensions from the means that carries the cutting head with respect to the guide ring. Locating the disposable blade housing in close proximity to the movement means reduces potential for physical interference and unintended distorted excursion of the microkeratome due to the disposable blade housing.

The disposable blade housing also includes a plaque, which is the portion of the blade housing directly in front of the blade. The plaque functions to partially compress the ocular globe immediately before contact by the blade, thereby regulating the depth and shape of incision.

In a preferred embodiment of the present invention the disposable blade housing is fabricated from a polymeric, composite or ductile ceramic material. The material must be flexible enough to be formed into a self-positioning, locking and releasable structure. The material of the disposable blade housing must also be capable of damping vibrations, maintaining dimensions, resisting deflections, and maintaining rigidity in order to produce a cut of satisfactory quality. Teflon is an example of an acceptable polymeric material. Teflon has an additional benefit of being self-lubricating, thereby eliminating the need for lubricants and decreasing the possibility of failure or binding of the moving parts. The plaque may be adjustable or non-adjustable. The plaque as shown in the drawings is not adjustable and may be of the type that provides a single predetermined shape and thickness of cut by the cutting blade.

In use, a guide ring is joined to an ocular globe and the microkeratome is joined to the guide ring to rotate across a plane substantially parallel to the top surface of the guide ring. The motor is actuated to oscillate blade and the microkeratome is moved across the guide ring to cut the ocular globe. When the procedure is complete, the microkeratome is removed and the blade housing, blade holder, and blade are disposed of. The motor and cutting head are retained for reuse. In an embodiment as depicted in FIGS. 2 and 5, the entire blade housing, blade holder, and blade are disposed of. The remaining components of the microkeratome are cleaned and fresh, unused components are reattached.

While the invention has been shown in only two of its forms, it should be apparent to those skilled in the art that it is not so limited, but is susceptible to various changes without departing from the scope of the invention.

What is claimed is:

1. A microkeratome for attachment to a guide ring secured to an ocular globe to perform lamellar keratotomy, the microkeratome comprising:

a blade assembly with a cutting edge;

a cutting head adapted to join to the guide ring and move in a plane substantially parallel to a surface of the guide ring, the cutting head having an integral compression surface for compressing the ocular globe and a blade slot adjacent the compression surface, wherein the cutting head closely receives the blade assembly such that the cutting edge protrudes through the blade slot toward the compression surface and the blade assembly is constrained to move substantially only along one axis, and wherein the cutting head has a lower portion releasably joined to an upper portion such that the blade assembly is held between the upper portion and lower portion;

a motor releasably attached to the cutting head to oscillate the blade assembly along the one axis; and wherein the upper portion has a longitudinal key and the lower portion has a longitudinal keyway adapted to receive the longitudinal key of the upper portion to hold the upper and lower portions together.

2. The microkeratome of claim 1 wherein the upper portion has a protrusion and the lower portion has an opening adapted to receive the protrusion and laterally restrain the lower portion with respect to the upper portion.

3. The microkeratome of claim 1 wherein the lower portion is made from a material that is more flexible than the material of e upper portion.

4. The microkeratome of claim 1 wherein the lower portion is made from a material selected from the group consisting of polymeric, composite, and ceramic materials.

5. The microkeratome of claim 1 wherein the cutting head has an overall height dimension and a height of the lower portion is less than one-third the dimension.

6. The microkeratome of claim 1 wherein the lower portion has a height dimension and the lower portion is located within two height dimensions of a point at which the lower portion joins the guide ring.

7. The microkeratome of claim 1 wherein the motor rotates a pin about a central axis and the blade assembly has a slot that receives the pin.

8. A microkeratome head for joining to a guide ring affixed to an ocular globe to perform a lamellar keratotomy, comprising:

a blade assembly;

an upper portion having a longitudinal key;

a blade housing adapted to join to the guide ring and move in a plane substantially parallel to a surface of the guide ring, the blade housing having a longitudinal keyway adapted to interlock with the key of the upper portion and hold the blade housing to the upper portion, the blade housing adapted to closely receive the blade assembly such that the blade assembly is restrained to move substantially along one axis;

a compression plaque on the blade housing adjacent the blade assembly for compressing the ocular globe as the blade housing is moved across the guide ring; and a motor releasably attached to the cutting head and adapted to oscillate the blade assembly along the one axis.

9. The microkeratome head of claim 8 wherein the upper portion has a protrusion and the blade housing has an opening to receive the protrusion and laterally restrain the blade housing relative to the upper portion.

10. The microkeratome head of claim 8 wherein the blade housing is made from a material that is more flexible than the material of the upper portion.

11. The microkeratome head of claim 8 wherein the blade housing is a material selected from the group consisting of polymeric, composite, and ceramic materials.

12. The microkeratome head of claim 8 wherein a height of the blade housing is less than one third a total height of the head.

13. The microkeratome head of claim 8 wherein the blade housing has a height dimension and the housing is within two height dimensions of a point at which the blade housing joins the guide ring.

14. A method of performing lamellar keratotomy on an ocular globe comprising the steps of:

providing a microkeratome having an upper portion, a lower portion, and a blade;

securing a guide ring to the ocular globe and joining the microkeratome to the guide ring;

moving the microkeratome across the guide ring to contact the blade with and cut the ocular globe;

removing the microkeratome from the guide ring and disposing of the lower portion and blade.

15. The method of claim 14 further comprising the step of joining another lower portion and blade to the upper portion.

\* \* \* \* \*